United States Patent [19]

Lane et al.

[11] Patent Number: 4,828,544
[45] Date of Patent: May 9, 1989

[54] CONTROL OF BLOOD FLOW

[75] Inventors: Rodney J. Lane, Cremorne; George R. Taylor, St. Ives; Gary W. Pace, Turramurra, all of Australia

[73] Assignee: Quotidian No. 100 PTY Limited, North Sydney, Australia

[21] Appl. No.: 864,699

[22] PCT Filed: Sep. 5, 1985

[86] PCT No.: PCT/AU85/00214
  § 371 Date: May 1, 1986
  § 102(e) Date: May 1, 1986

[87] PCT Pub. No.: WO86/01395
  PCT Pub. Date: Mar. 13, 1986

[30] Foreign Application Priority Data

Sep. 5, 1984 [AU] Australia ............................ PG6951
Feb. 28, 1985 [AU] Australia ............................ PG9513
Feb. 28, 1985 [AU] Australia ............................ PG9514

[51] Int. Cl.$^4$ .......................... A61F 2/48; F16K 15/20
[52] U.S. Cl. .......................................... 604/9; 128/79; 128/DIG. 25; 600/31; 623/1; 251/342
[58] Field of Search ................................... 604/8–10, 604/99, 256; 128/79, 1 R, 325, 326, 346, 344, 686, DIG. 25, 899; 251/341, 342, 348; 600/29–31; 623/1

[56] References Cited

U.S. PATENT DOCUMENTS

| 3,419,008 | 12/1968 | Plishner ............................ 128/1 R |
| 3,530,928 | 9/1970 | Swinney ............................ 251/342 |
| 3,534,771 | 10/1970 | Eyerdam ............................ 251/342 |
| 3,675,656 | 7/1972 | Hakim . |
| 3,699,957 | 10/1972 | Robinson . |
| 3,730,186 | 5/1973 | Edmunds, Jr. et al. . |
| 3,744,063 | 7/1973 | McWhorter et al. . |
| 3,750,194 | 8/1973 | Summers . |
| 3,758,073 | 9/1973 | Schulte ............................ 251/342 |
| 3,939,821 | 2/1976 | Roth . |
| 3,985,140 | 10/1976 | Harris ............................ 251/342 |
| 3,998,222 | 12/1976 | Shihata . |
| 4,044,401 | 8/1977 | Guiset . |
| 4,256,093 | 3/1981 | Helms et al. . |
| 4,428,365 | 1/1984 | Hakky ............................ 128/1 R |
| 4,475,899 | 10/1984 | Muller . |
| 4,501,263 | 2/1985 | Harbuck ............................ 128/1 R |
| 4,586,919 | 5/1986 | Taheri ............................ 604/9 |
| 4,587,954 | 5/1986 | Haber ............................ 128/1 R |
| 4,592,754 | 6/1986 | Gupte et al. ............................ 604/9 |
| 4,640,493 | 2/1987 | Dudzik ............................ 251/342 |

FOREIGN PATENT DOCUMENTS

| 1277083 | 5/1986 | Australia . |
| 2373272 | 7/1978 | France . |
| 1549315 | 7/1979 | United Kingdom . |
| WO8000302 | 3/1980 | World Int. Prop. O. . |
| WO84/02266 | 6/1984 | World Int. Prop. O. . |

Primary Examiner—Stephen C. Pellegrino
Assistant Examiner—Ralph Lewis
Attorney, Agent, or Firm—Lackenbach Siegel Marzullo & Aronson

[57] ABSTRACT

A blood flow control system comprising a primary arteriovenous fistula connecting a blood source to a vein, and a secondary fistula connected to the first fistual leading to a venous sink. A blood flow control device is engaged with the primary fistula so as to impede the flow therethrough, and is disposed between the secondary fistula and the vein, and it is actuated transcutaneously, whereby restriction of the blood flow through the primary fistula increases the flow of blood to the venous sink.

17 Claims, 9 Drawing Sheets

CONTROL OF BLOOD FLOW

FIELD OF INVENTION

This invention relates to the control of blood flow, and more particularly to the control of blood flow through an artery to vein fistula.

BACKGROUND ART

The problem of blood flow control through an arterio-venous fistula or a veno-venous fistula is described, inter alia, in the following publications:
1. "Pressure relations at site of an arterio-venous fistula": Emile Holman and Gerard Taylor, Angiology 3, 415–430, 1952.
2. "Portacaval H Graft : Relationships of shunt diameter, portal flow patterns and encephalopathy": James Sarfeh et al, Ann. Surg. Vol. 197 No. 4 422–426.

As stated by Holman and Taylor, the effects of a fistula depend in large measure upon its size, but even more significantly, upon the relationship of its size to the calibre of the vessels in which the fistula lies. Bearing directly upon this relationship is the concept that a vessel at any given point in the arterial tree has an arterial end pressure sufficient to overcome the peripheral resistance distal to it, the one being commensurate with the other. The larger the vessel, therefore, the greater will be the peripheral resistance of the capillary bed supplied by it, and consequently the greater must be the arterial end pressure to overcome it.

Also, the larger the vessels between which a fistula lies, the greater will be the difference between the low pressure of the central venous bed and the high peripheral resistance of the capillary bed distal to the fistula, thus increasing the tendency for blood to avoid the capillary bed and to flow into the central venous bed.

Moreover, the larger the artery in which the fistula lies, the higher will be the artery end pressure directing blood through the fistula into the large central reservoir of low venous pressure with a corresponding increase in velocity of blood through the fistula. Given a uniform size of fistula, the nearer to the heart this fistula lies in the main arterial tree, the greater will be the volume of blood pouring through it.

Thus, the work of Holman and Taylor was, in essence, concerned with the location and size of a fistula rather than upon the control of flow of blood through the fistula.

The work of Sarfeh et al was concerned with the use of portacaval H-grafts of different diameters and not with the control of blood flow through the grafts.

Although neither of the abovementioned publications refers to any device for controlling the flow of blood through a fistula, an implantable device for restricting the flow of blood through a major blood vessel such as an artery is disclosed in U.S. Pat. No. 3,730,186 of Edmunds et al.

The Edmunds device consists of an inflatable, flexible annulus, generally circular in shape but not a closed circle, which has a non-distensible outer wall so that upon inflation all distention or expansion is inward.

The Edmunds device is placed around an artery or other blood vessel and the ring is then closed by suturing together pre-formed tabs attached to the annulus, or by suturing together the ends of an overlaping tape to hold the vessel firmly.

Upon inflation, inward distention of the inflatable annulus constricts the vessel and flow of blood therethrough is accordingly restricted. Inflation and deflation are effected through a self-sealing hollow bulb and a non-distensible tube connecting the bulb to the interior of the inflatable annulus.

Although U.S. Pat. No. 3,730,186 does disclose an implantable adjustable extravascular occluding band adapted to restrict the flow of blood, the only application described in the specification is concerned with the control of blood flow through an artery and does not relate to the diversion of blood flow from arteries between veins and venous sinks.

In general terms, blood flows from an artery through an organ (e.g. liver) which may be considered as an venous sink and then back to a vein. When the normal blood flow system ceases to operate correctly, various kinds of vascular problems may arise.

For example, in recent years, it has become increasingly clear that very frequently erectile impotence is associated with penile vascular problems, although they may not be the only contributive factors to the symptom which is often multi-determined.

For the sake of brevity, the invention will be described in relation to vasculogenic impotence but it is to be understood that the invention is not limited thereto as its principles may be applied to any situation in which the flow of blood is to be controlled.

Penile arterial inflow is through three pairs of arteries (dorsal artery, deep artery and bulbourethral artery) which are branches of the internal pudendal artery. There is great variation in their branching, the position at which they pierce the tunica albuginea and how they communicate. The glands receives its main arterial supply from the dorsal artery, the cavernous bodies from the paired deep arteries. There are arteriovenous shunts at many levels of arterial branching-outside as well as inside the tunica albuginea.

The von Ebner pads protrude not only in to the small penile arteries as originally described, but also occur in almost all parts of the arterial tree supplying the erectile tissue as far back as the penile artery after it passes through the urogenital diaphragm. Their exact function is unknown, although they may be involved in flow regulation. The venous drainage mainly takes place through the systems of the deep dorsal vein and the deep central veins.

There are theories as to the vascular mechanisms of penile erection, but the exact mechanism is obscure as no theory can encompass all the facts and clinical observations. Both inflow and outflow (venous drainage) regulatory mechanisms appear to be involved simultaneously.

The prior art contains various proposals for overcoming erectile impotence. For example the Jonas penile prothetis consists of silver wires embedded in a silicone tube. The Finney penile implant consists of a hinged flexirod device made of clear silicone. Other devices include the Scott prosthesis which is a totally implantable device using inflatable silastic cylinders placed inside each corpus cavernosum and connected by silastic tubing to a pumping mechanism implanted in the scrotal pouch, the fluid for inflation being provided by a reservoir implanted behind the rectus muscle.

In 1975 Small and Carrion reported the development of a silastic prosthesis which consisted of two semi-rigid moulded silicone rods implanted side by side in the matrix of each corpus cavernosum.

None of the aforementioned prothesis has been particularly successful in overcoming erectile impotence as not one overcomes the problem of impaired circulation.

Other vascular disorders are well known and their correction along with that for vasculogenic impotence necessitates the establishment of an alternative vascular path.

Other implantable devices for temporarily controlling the flow of blood or other body fluids are known.

A typical example of such an implantable device is the so-called urinary incontinence prosthesis which has an inflatable urethral occluder that is connected by tubing to a reservoir bulb. The bulb has a squeeze deformable valve operative to allow flow of fluid from the bulb to the occluder and, when squeezed, to allow flow of fluid from the occluder to the reservoir bulb.

Usually, the reservoir bulb and the deformable valve are located in the scrotum so that a squeeze action can be easily applied to the bulb to force fluid through the valve to the occluder. When the occluder is to be relaxed, the valve is squeezed whereupon it opens to allow the fluid to flow back into the reservoir bulb.

The reservoir and valve are so located in the body as to be readily manipulated by the fingers. There is a need for a normally closed valve that is able to pass fluid from the reservoir when the reservoir is squeezed (or otherwise deformed) by pressure applied through the skin and which can be easily opened to allow the fluid to flow back into the reservoir.

One such valve which is disclosed in U.S. Pat. No. 3,758,073 consists of a valve body having an internal flow cavity bounded by a peripheral wall. An inlet port which could be connected to the occluder or balloon of the above described devices communicates with the flow cavity through an opposite end wall. A flow control member has a central aperture in a base that bears against the opposite end wall, the aperture being aligned with the outlet port.

A valve seat formed as an annular ring about the aperture in the flow control member is covered by a flexible diaphragm that is supported by the periphery of the flow control member. The central portion of the diaphragm is imperforate so that when the diaphragm is against the valve seat, the valve is normally closed. A plurality of perforations formed in the diaphragm outside the central imperforate region provide fluid communication across the diaphragm.

When it is desired to open the valve, the body is squeezed to deform the diaphragm which lifts from the valve seat so that fluid can flow through the perforations and then through the outlet to the reservoir so as to depressurize the occluder or balloon. The flexibility of the diaphragm is such that when flow is to be reversed, pressure on the reservoir will lift the central portion of the diaphragm from the valve seat.

A disadvantage of the above kind of valve is that the opening pressure is not positively applied to the valve diaphragm, but, rather it is the deformation of the valve body which leads to wrinkling of the diaphragm and it is the degree and manner of wrinkling which leads to the displacement of the valve diaphragm from the valve seat.

DISCLOSURE OF INVENTION

It is an object of this invention to provide a blood flow control system which can be used to divert blood flow into a venous sink in order to overcome a defect in the ordinary vascular system.

According to the invention, there is provided a blood flow control system comprising a primary arterovenous fistula having a secondary fistula leading to a venous sink and blood flow control means engaged with the primary fistula between the secondary fistula and the vein whereby restriction of the blood flow through the primary fistula by the venous sink.

The invention also provides an implantable device for controlling the flow of blood through a primary arterovenous fistula so as to control the flow of blood to a venous sink through a secondary fistula connected to the primary fistula, comprising inflatable pressure means adapted to engage the primary fistula between the secondary fistula and the vein, pump means in communication with the pressure means adapted to inflate the pressure means whereby the pressure means restricts the flow of blood through the primary fistula and means for deflating the pressure means.

According to another aspect of the invention there is provided a normally closed valve which can be opened by the application of a compressive force on the exterior of the valve, comprising:

(i) a valve body defining a valve chamber
(ii) an inlet to and an outlet from the chamber,
(iii) a valve seat member having:
 (a) an annular body portion held captive within the chamber by the valve body,
 (b) a bore in communication with the inlet and extending to the outlet,
 (c) an annular valve seat around the outlet end of the bore, and,
 (d) a plunger supported within the bore and extending towards the outlet, and,
(iv) a valve member overlying and normally closing the annular valve seat, said valve member being coupled to the plunger so that when the valve body is distorted by the application of an external compressive force at or adjacent to the inlet, the valve seat member is so distorted that the plunger moves towards the outlet whereby the valve member is moved away from the valve seat so as to place the outlet in communication with the inlet.

Preferably, a portion of the valve member is secured to the valve seat and a hinge is formed in the valve member adjacent to the zone of fixation to the valve seat.

According to yet another aspect of the invention there is provided a normally closed valve which can be opened by the application of a compressive force on the exterior of the valve, comprising:

(i) a valve body defining a valve chamber,
(ii) an inlet to and an outlet from the valve chamber,
(iii) a valve seat member disposed across the valve chamber and having a bore in communication with the inlet and selectively in communication with the outlet,
(iv) a perforated support member positioned in the valve chamber between the outlet and the valve seat member and having a valve plunger extending therefrom adapted to engage and close the bore of the valve seat member, the arrangement being such that when the valve body is distorted by the application of an external compressive force between the perforated support member and the valve seat member, the valve seat moves away from the plunger towards the inlet whereby the outlet is placed in communication with the inlet.

BRIEF DESCRIPTION OF THE DRAWINGS

In order that the invention may be more readily understood and put into practical effect, reference will now be made to the accompanying drawings in which.

BEST MODE OF CARRYING OUT THE INVENTION

In the embodiment of the invention shown in the drawings, the blood flow control device is used to control the flow of blood to the penis. It is to be understood, however, that the device of the invention may be used to control the flow of blood to any other venous sink.

Figure 1:
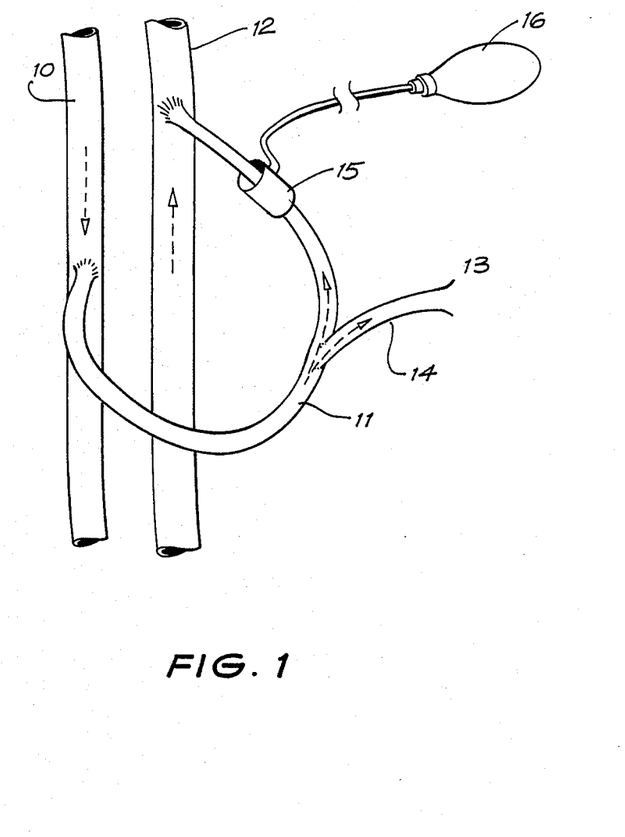
FIG. 1 is a schematic view of a blood flow control system according to one embodiment of the invention.

The blood flow control system shown in FIG. 1 is, in essence a vascular tap which includes a primary fistula 11 that is connected between an artery 10 and a vein 12. A secondary fistula 14 leads to a venous sink 13 which may be any organ of the body such as the penis or the liver. A blood flow control means 15 is engaged with primary fistula 11 between the secondary fistula 14 and the vein 12. When the control device 16 is actuated the blood flow control means 15 restricts the flow of blood through the upper portion of the primary fistula 11 to increase the flow of blood to the venous sink 13 through the secondary fistula 14.

Figure 2:
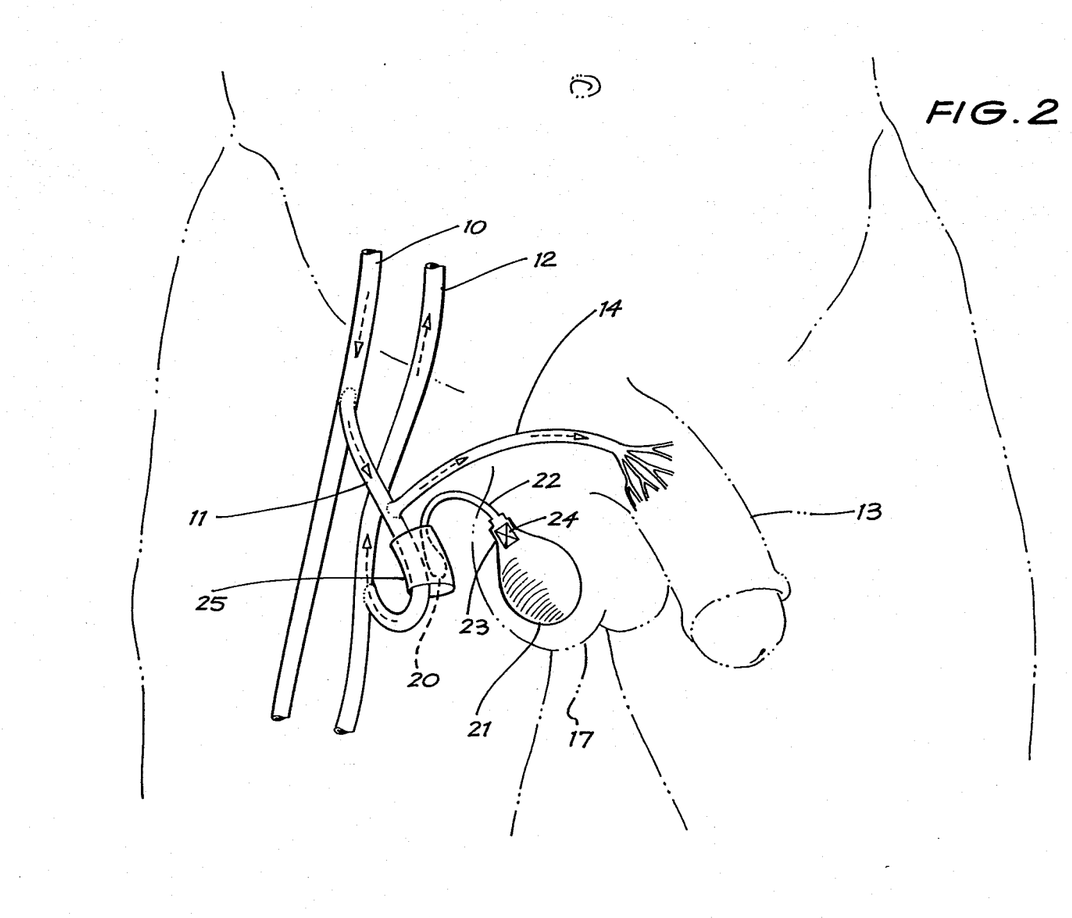
FIG. 2 is an anterior view of the right groin of a male showing a blood flow control device according to one embodiment of the invention acting upon a primary fistula.

FIG. 2 is an anterior view of the right groin showing a fistula 11 connected between the femoral artery 10 and the femoral vein 12. Normally, blood flows down the femoral artery 10 through the primary fistula 11 and returns to the heart through the femoral vein 12. A secondary fistula 14 connected to the primary fistula 11 directs blood flow to the penis 13.

The blood flow control device shown in the FIG. 2 includes an inflatable pressure means or balloon 20 which is made from any convenient implantable material and a manually compressible balloon 21 implated within the scrotum 17. The balloon 21 is connected to the balloon 20 through a tube 22 and has a two-way valve 23 at its mouth 24.

Figures 3, 4:
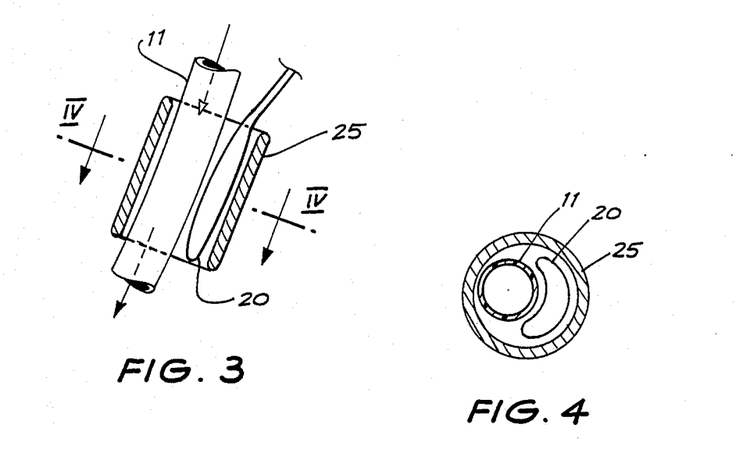
FIG. 3 is a partially sectioned, enlarged view of the inflatable pressure means of the blood flow control device shown in FIG. 2 with the pressure means deflated.
FIG. 4 is a view taken along lines III—III of FIG. 3
Figure 5:
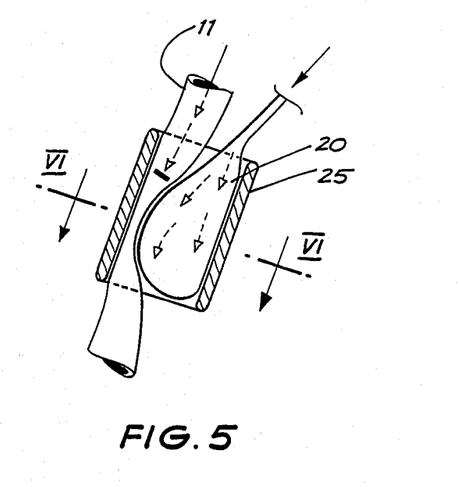
FIG. 5 is a view corresponding to FIG. 3 with the pressure means inflated.
Figure 6:
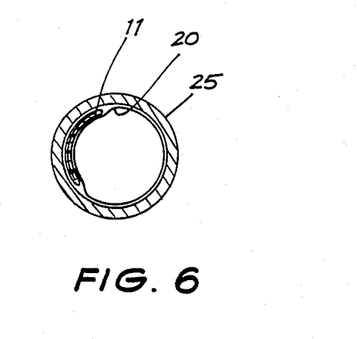
FIG. 6 is a view taken along lines V—V of FIG. 5

As can be seen in FIGS. 3 and 4, the balloon 20 is held in position against the primary fistula 11 by a gortex tube 25. When the ballon 20 is deflated (as shown in FIG. 3), blood flow through the primary fistula 11 is not impeded. When the balloon 20 is inflated by compressing the balloon 21, it presses against the primary fistula 11 to close or substantially close the fistula 11 so that blood flow from the femoral artery 10 is diverted through the secondary fistular to the penis 13.

It will be appreciated that the blood flow control device of the invention creates an artificial system which allows normal blood flow through the primary fistula 11. The device is used for only short periods of time—say 20 minutes—to avoid thrombosis. As the entire device is implanted, it must be made from implantable materials. The valve 23 in the scrotum 17 is two-way to permit inflation and deflation of the balloon 20.

Figure 7:
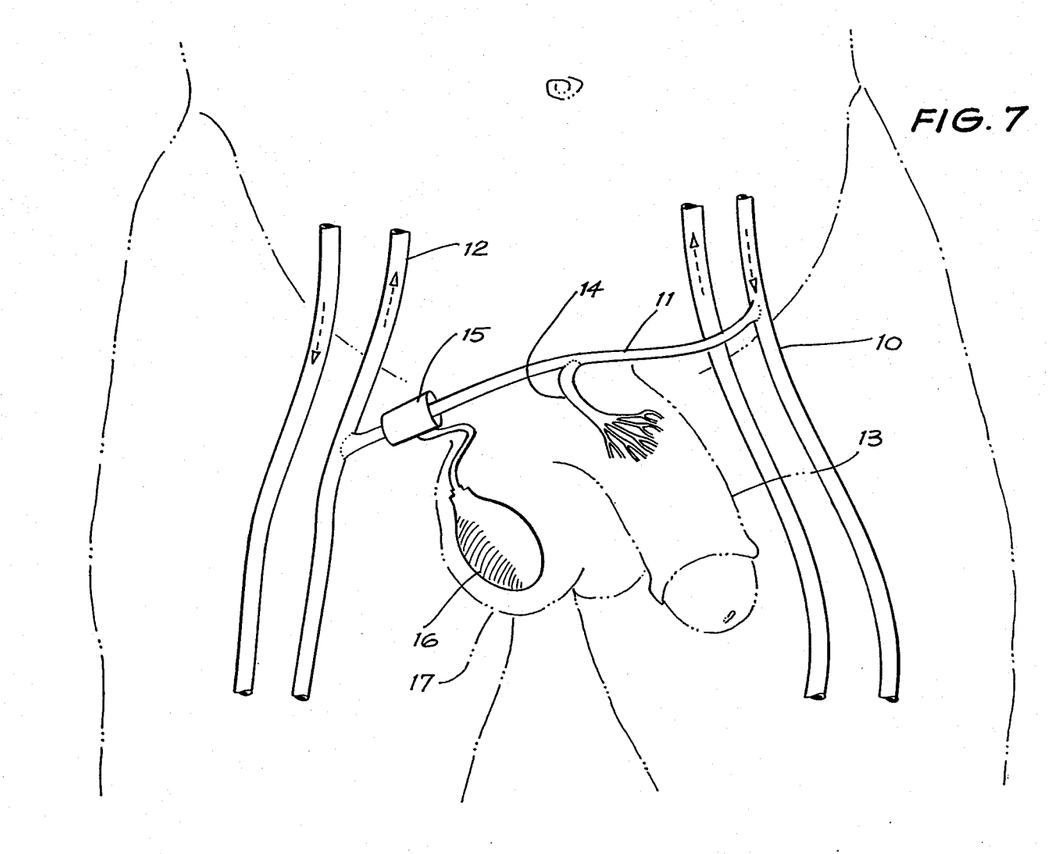
FIG. 7 is a view similar to FIG. 2 showing a crossover femoro-femeral fistula.

FIG. 7 shows an alternative arrangement for the blood control system of the invention utilizing a crossover fistula 11 which is connected between the artery 10 in the left leg and the vein 12 in the right leg. Otherwise the arrangement is the same as that shown in FIG. 2.

Figure 8:
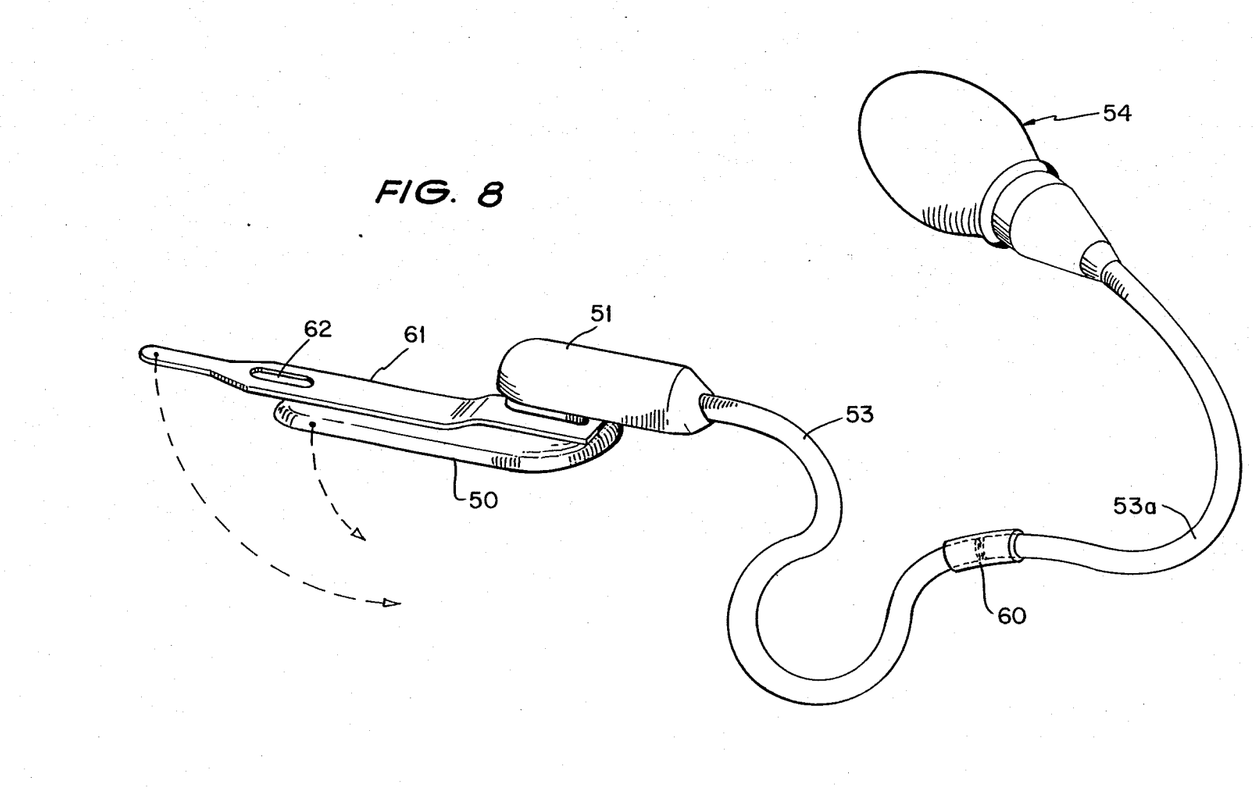
FIG. 8 is a perspective view of an implantable device for controlling the flow of blood according to one embodiment of the invention.
Figure 9:
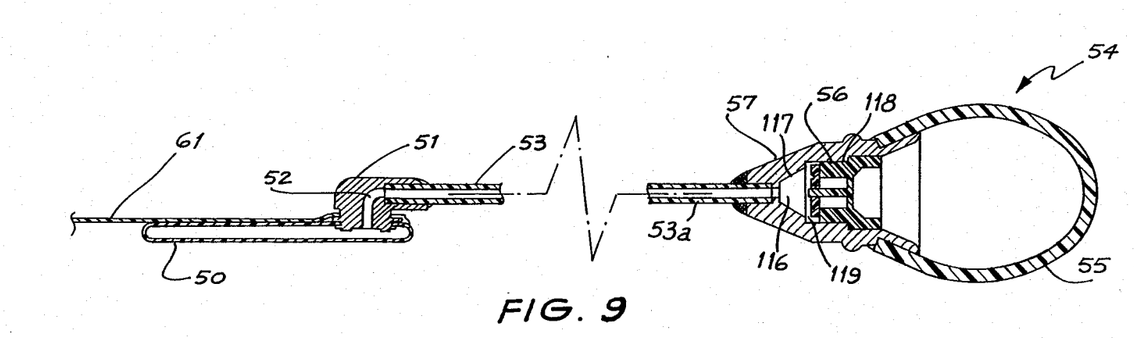
FIG. 9 is a cross-sectional view of an implantable device shown in FIG. 8.

The blood flow control device shown in FIGS. 8 and 9 includes an inflatable pressure means or balloon 50 mounted on a balloon connector 51 having a passageway 52 in communication with the interior of the balloon 50 and a connecting tube 53. A coupling 60 connects connecting tube 53 to connecting tube 53a.

The other end of the connecting tube 53a is connected to a pump assembly 54 which includes a compressible balloon 55, a valve 56 and a valve body 57.

Figure 10:
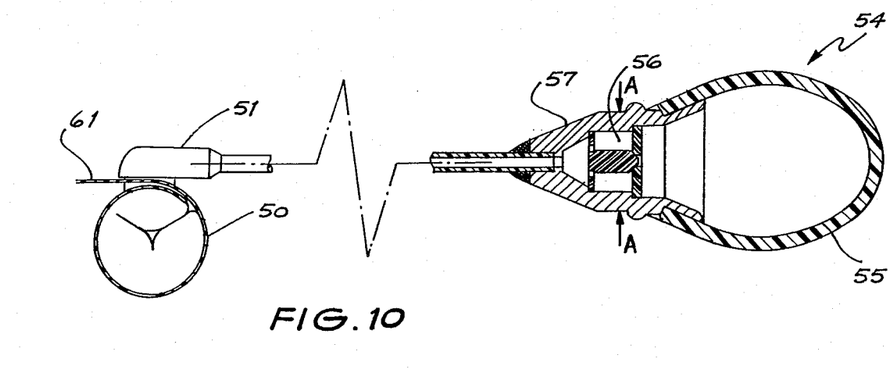
FIG. 10 is a view similar to FIG. 9 showing an alternative pump assembly and the balloon assembly in its inflated condition.

A strap 61 is connected to the balloon connector 51 above the balloon 50 and has an aperture 62 through which is fed the connecting tube 53 and the connector 51 to be locked in the position shown in FIG. 10.

An alternative pump assembly is shown in FIG. 9 which also shows the balloon assembly inflated and the strap locked in position. The same numerals are used in respect of similar components and further description will be given in relation to FIG. 13.

Figure 11:
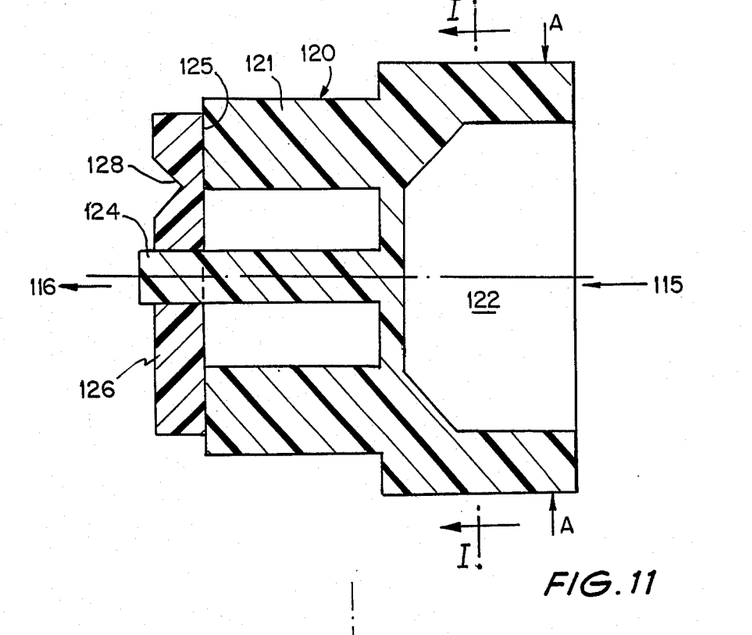
FIG. 11 is a cross-sectional view of the valve shown in FIG. 9.

The valve 56 of FIG. 9 is shown in greater detail in FIGS. 10 and 11 and has a body of silicone or other implantable flexible material which defines a valve chamber 57 as indicated in FIG. 9. An inlet 115 is connected to the reservoir 55 of an implantable blood flow control device. Outlet 116 is formed as a conical chamber which has a peripheral flange 118 by means of which it is secured to valve 56 (see FIG. 9). The outlet 116 is connected to the balloon 50 of the above described blood flow control device.

Figure 12:
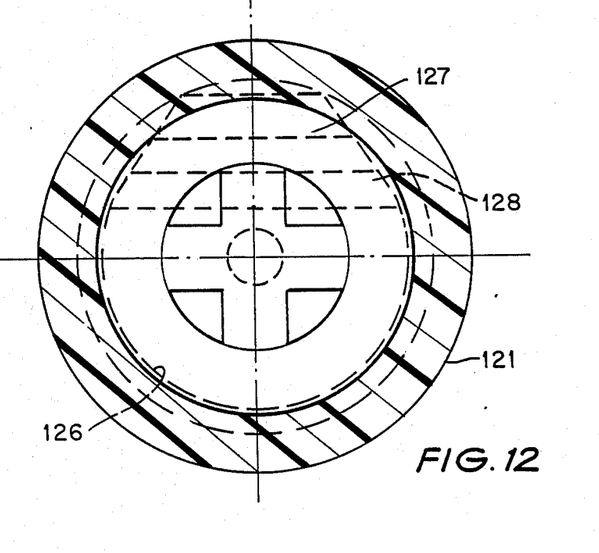
FIG. 12 is a view taken along the lines I—I of FIG. 11.

Within the valve chamber is a valve seat member 120 which has an annular body portion 121 that is held captive by the valve body. The rear wall and adjacent portions of the valve body are initially distorted so that the valve seat member 120 may be positioned within the chamber. The bore 122 of the valve seat member 120 is in communication with the inlet 115 and extends towards the outlet 116. Within the bore 122 there is an annular valve seat 125 around the bore 122. A valve member or diaphragm 126 overlies and normally closes the valve seat 125. The diaphragm 126 is secured to and movable by the plunger 124. As can be seen in FIG. 12, the diaphragm 126 has a non-circular zone 127 by means of which it is secured to the valve seat 125 by a suitable adhesive. A hinge 128 is positioned adjacent to the zone of fixation 127.

In operation, fluid from the reservoir can be forced into the inlet 115 and through the bore 122 where its pressure lifts the valve diaphragm 126 so that the fluid can pass through the outlet 116. As soon as pressure on the reservoir is relaxed, the diaphragm 126 returns to its original position in which it seals against the valve seat 125.

When fluid is to be returned to the reservoir, the valve body is squeezed in the direction of arrows A whereupon the valve seat member 120 is distorted to move the plunger 124 towards the outlet 116 and in so doing lifts the valve diaphragm 126 from the valve seat 125.

Figure 13:
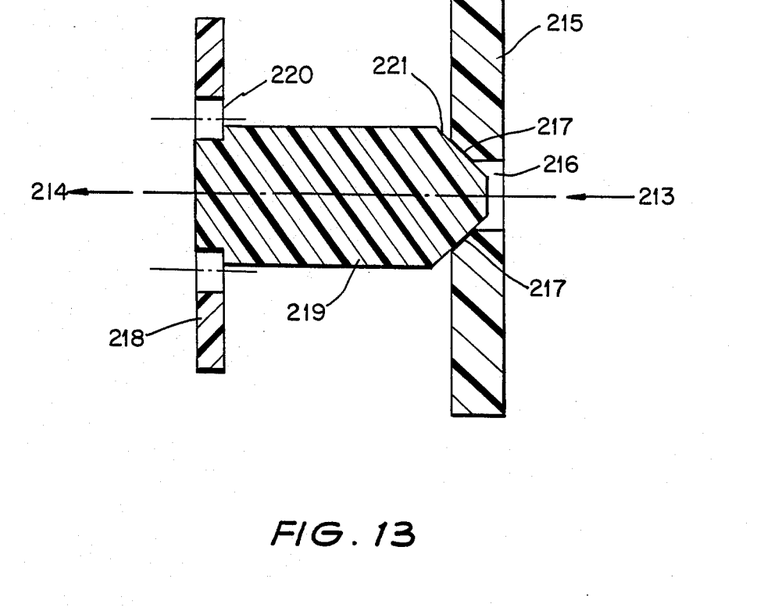
FIG. 13 is a cross-sectional view of the valve assembly shown in FIG. 10.

The valve shown in FIG. 13 has a body (not shown) of silicone or other implantable flexible material which defines a valve chamber. In this instance, the body is of tubular form and has an inlet 213 and an outlet 214.

Within the valve chamber there is a valve seat member 215 which is disposed transversely of the valve chamber. The valve seat member 215 has a bore 216 in communication with the inlet 213 and a conical portion 217 which faces the inlet 213.

A support member 218 having perforations 220 is transversely disposed in the valve cavity between the outlet 214 and the valve seat member 215. A valve plunger 219 extending from the support member 218 is adapted by means of conical face 221 to engage and close the bore 216 of the valve seat member 215.

The inlet 213 is connected to the reservoir 55 of the implantable blood flow control device shown in FIG. 10 and the outlet 214 is connected to the balloon 50 of that device. In operation, fluid from the reservoir 55 is forced into the inlet 213 and through the bore 216 where its pressure lifts the plunger 219 so that fluid can pass through the perforations 220 of the support member 218 to the outlet 214. As soon as pressure on the reservoir 55 is relaxed the plunger 219 will return to its original position in which it seals the bore 216. Pressure then present at the outlet 214 will retain the plunger 219 in its closed position.

When fluid is to be returned to the reservoir 55, the valve body 210 is squeezed in the direction of the arrows A (see FIG. 10) whereupon the valve seat member 215 is distorted to move away from the plunger 219 towards the inlet 213 and in so doing placed the outlet 214 in communication with the inlet 213.

Figure 14:
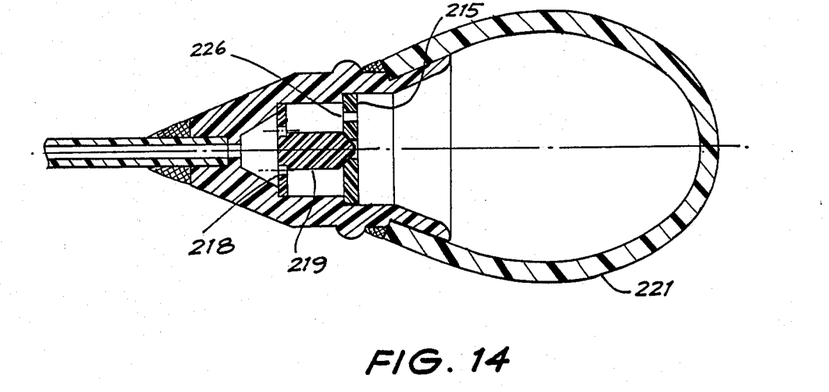
FIG. 14 is a cross-sectional view of an alternative pump assembly for the implantable device shown in FIG. 10.

The valve shown in FIG. 14 is substantially similar to that shown in FIG. 13 and the same numerals are given to the equivalent components. In this instance, the valve seat member 215 has a small perforation 226 for controlled flow of fluid back into the balloon 221. This arrangement has the advantage that by adjusting the diameter of the perforation 226 and the viscosity of the fluid, the valve will automatically return to its deflated position and thus control the duration that blood is diverted to the venous sink.

Figure 15:
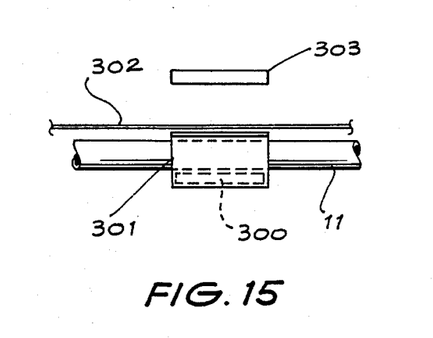
FIG. 15 is a side-elevational view, partly cut away, of a control device for use with the blood control system shown in FIG. 1 and 7, and, FIG. 16 is an end view of the control device shown in FIG. 15.
Figure 16:
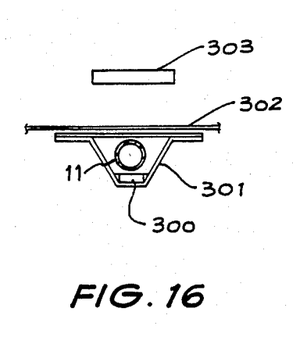

FIGS. 15 and 16 show an alternative flow control arrangement in which a magnet 300 is secured to the primary fistula 11 by means of a gortex cuff 301. As can be seen in FIG. 15, the magnet 300 is located on the side of the fistula remote from the epidermis 302. An exterior magnet 303, when positioned on or near the epidermis 302, draws the magnet 300 towards it so as to partially restrict the internal lumin of the fistula 11. Other external actuators such as R. F. signals could be employed.

The above described blood flow control systems may be used to control blood flow through an arterio-venous fistula so as to control or orgment the flow through extra corporeal circuits. For example, if the blood flow control system of the invention is employed as an arterio-venous fistula for haemodialysis patents, the device could be used for increased blood flow during dialysis and for decreased fistula flow during the off-dialysis period. The same concept could, in principle be used for any extra corporeal treatment procedure (for example plasmophoresis) as easily as it could be applied intra corporeally.

Various modifications may be made in details of the invention without departing from its scope and ambit.

We claim:

1. A blood flow control system comprising a primary arteriovenous fistula fluidly connecting a blood source to a vein, a secondary fistula fluidly connected to said primary fistula leading to a venous sink; and blood flow control means engaged with the primary fistula so as to impede the flow therethrough, and disposed between the secondary fistula and the vein and being actuated transcutaneously; whereby restriction of the blood flow through the primary fistula by the blood flow control means increases the flow of blood to the venous sink.

2. A blood flow control system according to claim 1, wherein the blood flow control means includes pressure means capable of engaging and constricting the primary fistula, pump means in fluid communication with the pressure means adapted to inflate the pressure means so as to restrict the flow of blood from the primary fistula to the vein and means for deflating the pressure means.

3. A blood flow control system according to claim 2 wherein the pump means includes a balloon connected through a valve to said pressure means.

4. A blood flow control system according to claim 3 wherein the valve is adapted to provide controlled back-flow so that the blood flow restriction of the primary fistula decreases over a pre-determined period.

5. A blood flow control system according to claim 3 wherein the valve includes a valve seat and a flexible diaphragm within a valve body and wherein the valve is opened by deforming the valve body.

6. A blood flow control system according to claim 3 wherein the valve is normally closed and can be opened by the application of a compressive force on the exterior of the valve, said valve comprising:
(i) a valve body defining a valve chamber,
(ii) an inlet to and an outlet from the chamber,
(iii) a valve seat member disposed across the valve chamber and having a bore in communication with the inlet and selectively in communication with the outlet,
(iv) a perforated support member positioned in the valve chamber between the outlet and the valve seat member and having a valve plunger extending therefrom adapted to engage and close the bore of the valve seat member, the arrangement being such that when the valve body is distorted by the application of an external compressive force between the perforated support member and the valve seat member, the valve seat moves away from the plunger towards the inlet whereby the outlet is placed in communication with the inlet.

7. A blood flow control system according to claim 6 wherein the valve seat member is perforated so to provide controlled flow of fluid back to the valve body.

8. A blood flow control system according to claim 3 wherein the valve is normally closed and can be opened by the application of a compressive force on the exterior of the valve, said valve comprising:
 (i) a valve body defining a valve chamber,
 (ii) an inlet to and an outlet from the chamber,
 (iii) a valve seat member having:
  (a) an annular body portion held captive within the chamber by the valve body
  (b) a bore in communication with the inlet and extending to the outlet,
  (c) an annular valve seat around the outlet end of the bore, and
  (d) a plunger supported within the bore and extending towards the outlet, and,
 (iv) a valve member overlying and normally closing the annular valve seat, said valve member being coupled to the plunger so that when the valve body is distorted by the application of an external compressive force at or adjacent to the inlet, the valve seat member is so distorted that the plunger moves towards the outlet whereby the valve member is moved away from the valve seat so as to place the outlet in communication with the inlet.

9. A blood flow control system according to claim 8 wherein a portion of the valve member is secured to the valve seat and a hinge is formed in the valve member adjacent to the portion secured to the valve seat.

10. A blood flow control system according to claim 1 wherein the blood flow control means comprises magnetic means secured to the primary fistula at a location remote from the epidermis adapted to squeeze the primary fistula under the influence of an exterior magnet.

11. An implantable device for controlling the flow of blood to a vein through a primary arteriovenous fistula and a venous sink through a secondary fistula connected to the primary fistula, comprising inflatable pressure means adapted to engage the primary fistula between the secondary fistula and the vein, pump means in communication with the pressure means adapted to inflate the pressure means, whereby the pressure means restricts the flow of blood through the primary fistula and increases the flow of blood to the venous sink, and means for deflating the pressure means, wherein the means for deflating the pressure means includes a valve that can be opened by the application of a compressive force on the exterior valve, said valve comprising:
 (i) a valve body defining a valve chamber
 (ii) an inlet to and an outlet from the chamber,
 (iii) a valve seat member disposed across the valve chamber and having a bore in communication with the inlet and selectively in communication with the outlet,
 (iv) a perforated support member positioned in the valve chamber between the outlet and the valve seat member and having a valve plunger extending therefrom adapted to engage and close the bore of the valve seat member, the arrangement being such that when the valve body is distorted by the application of an external compressive force between the perforated support member and the valve seat member, the valve seat moves away from the plunger towards the inlet whereby the outlet is placed in communication with the inlet.

12. An implantable device for controlling the flow of blood to a vein through a primary arteriovenous fistula and a venous sink through a secondary fistula connected to the primary fistula, comprising inflatable pressure means adapted to engage the primary fistula between the secondary fistula and the vein, pump means in communication with the pressure means adapted to inflate the pressure means, whereby the pressure means restricts the flow of blood through the primary fistula and increases the flow of blood to the venous sink, and means for deflating the pressure means, wherein the means for deflating the pressure means includes a valve that can be opened by the application of a compressive force on the exterior valve, said valve comprising:
 (i) a valve body defining a valve chamber
 (ii) an inlet to and an outlet from the chamber,
 (iii) a valve seat member having:
  (a) an annular body portion held captive within the chamber by the valve body
  (b) a bore in communication with the inlet and extending to the outlet,
  (c) an annular valve seat around the outlet end of the bore, and
  (d) a plunger supported within the bore and extending towards the outlet, and
 (iv) a valve member overlying and normally closing the annular valve seat, said valve member being coupled to the plunger so that when the valve body is distorted by the application of an external compressive force at or adjacent to the inlet, the valve seat member is so distorted that the plunger moves towards the outlet whereby the valve member is moved away from the valve seat so as to place the outlet in communication with the inlet.

13. A normally closed valve which can be opened by the application of a compressive force on the exterior of the valve, comprising:
 (i) a valve body defining a valve chamber,
 (ii) an inlet to and an outlet from the chamber,
 (iii) a valve seat member having:
  (a) an annular body portion held captive within the chamber by the valve body,
  (b) a bore in communication with the inlet and extending to the outlet,
  (c) an annular valve seat around the outlet end of the bore, and
  (d) a plunger supported within the bore and extending towards the outlet, and,
 (iv) a valve member overlying and normally closing the annular valve seat, said valve member being coupled to the plunger so that when the valve body is distorted by the application of an external compressive force at or adjacent to the inlet, the valve seat member is so distorted that the plunger moves towards the outlet whereby the valve member is moved away from the valve seat so as to place the outlet in communication with the inlet, wherein a portion of the valve member is secured to the valve seat and a hinge is formed in the valve member adjacent to the portion secured to the valve seat.

14. A blood flow control system, comprising: a first blood flow path fluidly connecting a blood source to a vessel, a second blood flow path fluidly connecting said first blood flow path to a venous sink, and blood flow control means engaged with said first blood flow path between said second blood flow path and said vessel, said blood flow control means including an inflatable cuff adapted to constrict said first blood flow path thereby to restrict the flow of blood through said first blood flow path an to increase the flow of blood through said second blood flow path, means for inflating the cuff and means for deflating the cuff, said blood flow control means being fully implanted within a body and said inflating and deflating means being operable by pressure applied transcutaneously.

15. The blood flow control system according to claim 14, wherein said first blood flow path is a fistula.

16. The blood flow control system according to claim 14, wherein said second blood flow path is a fistula.

17. The blood flow control system according to claim 14, wherein said first and second blood flow paths are fistulas.

* * * * *